United States Patent [19]

Bemurat

[11] Patent Number: 5,111,830
[45] Date of Patent: May 12, 1992

[54] PACEMAKER LEAD WITH AUXILIARY STIMULATION POLE

[76] Inventor: Marc Bemurat, 20 Allées du Bicon, 33850 Leognan, France

[21] Appl. No.: 619,459

[22] Filed: Nov. 29, 1990

[51] Int. Cl.⁵ .............................................. A61N 1/05
[52] U.S. Cl. ................................. 128/786; 128/419 P
[58] Field of Search ................. 128/783, 78 A, 785, 128/786, 419 P

[56] References Cited

U.S. PATENT DOCUMENTS

| | | | |
|---|---|---|---|
| 5,014,71 | 5/1991 | Hirschberg | 128/785 |
| 3,437,091 | 4/1969 | Jerushalmi | 128/404 |
| 3,871,382 | 3/1975 | Mann | 128/419 P |
| 3,924,639 | 12/1975 | Hess | 128/418 |
| 4,538,623 | 9/1985 | Proctor et al | 128/784 |
| 4,602,645 | 7/1986 | Barrington | 128/786 |

FOREIGN PATENT DOCUMENTS 2537874  6/1984  France.
656313   6/1986  Switzerland.

Primary Examiner—William E. Kamm
Assistant Examiner—Scott M. Getzow
Attorney, Agent, or Firm—Roylance, Abrams, Berdo & Goodman

[57] ABSTRACT

A pacemaker lead of the type comprising a flexible cord formed of at least one spiralled electric conductor and surrounded by an insulating material sheath and connected, at one end of the lead, to a connection head removable from the pacemaker and, at the other end, to a stimulation electrode device, said lead being characterized in that at a defined position of the flexible cord said sheath has an interruption of continuity making said spiralled conductor accessible from the outside, said interruption of continuity being able to be sealingly insulated from the outside by a mobile means.

7 Claims, 1 Drawing Sheet

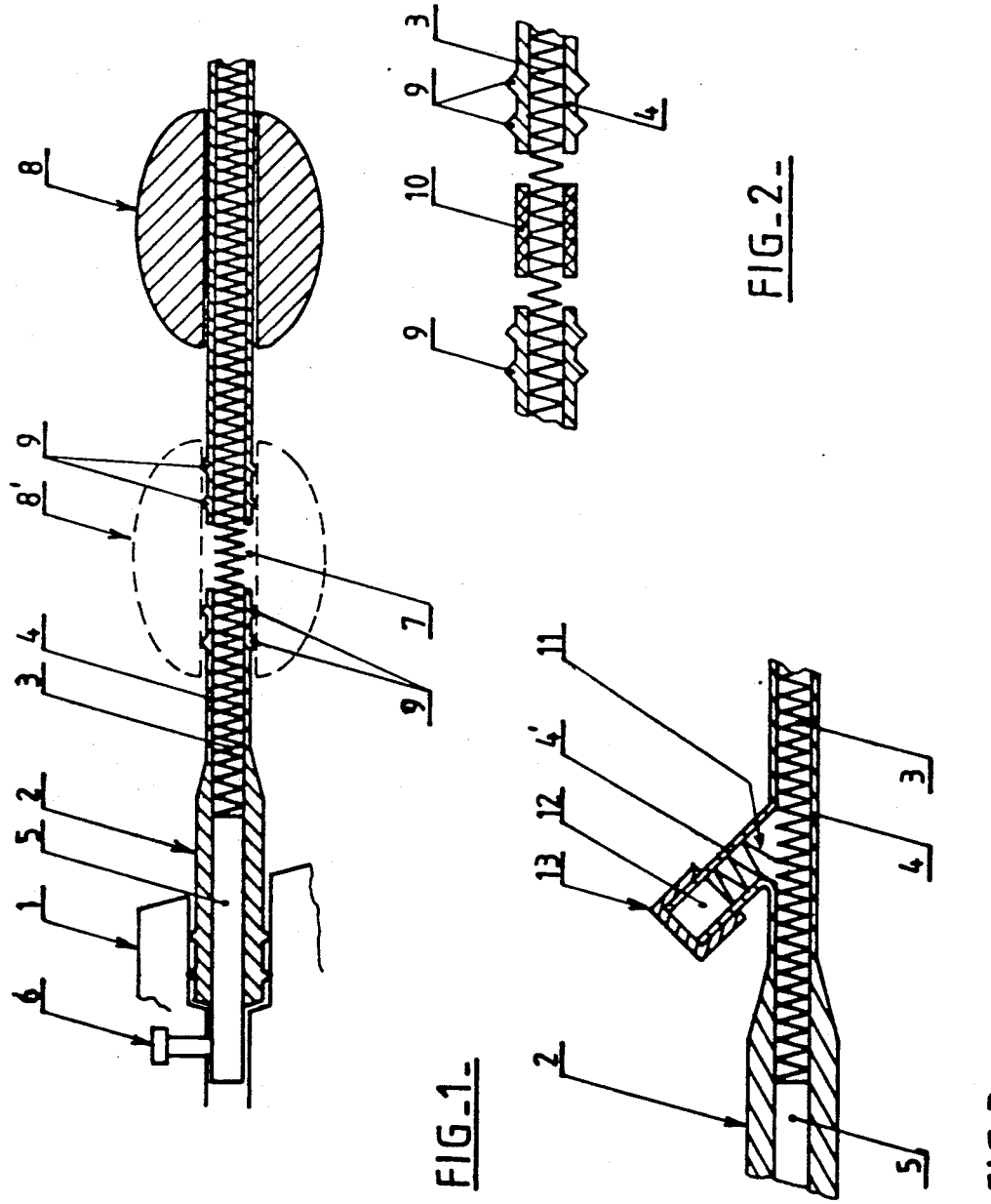

PACEMAKER LEAD WITH AUXILIARY STIMULATION POLE

BACKGROUND OF THE INVENTION

The present invention relates to pacemaker stimulation leads.

At the present time, in a stimulation lead, only the head of the lead may receive electric stimulation. The head of the lead being inserted into the pacemaker, it is only accessible when the lead is disconnected and removed from the pacemaker.

During replacement of a pacemaker, the stimulation lead is practically always kept. The operation consists in loosening a screw providing pacemaker lead contact, removing the lead from the pacemaker, inserting it into the new pacemaker and tightening the screw on the head of the lead and finally reimplanting the lead and pacemaker under the skin.

This operation may take several tens of seconds.

Now, as soon as the screw is loosened, the patient is no longer stimulated. That is not serious if the patient keeps his own spontaneous cardiac rhythm, but some patients, called "dependent" have no spontaneous cardiac rhythm. The patient is then in cardiac arrest from the moment when the screw of the old pacemaker is loosened until the moment when the screw of the new pacemaker again provides contact with the stimulation lead.

In a dependent patient, this operation is difficult, even dangerous.

The object of the invention is to overcome this serious drawback by providing a lead designed so as to ensure continuity of the stimulation of the patient, particularly during replacement of his pacemaker.

SUMMARY OF THE INVENTION

For this, the invention provides a pacemaker lead of the type comprising a flexible cord formed of at least one spiralled electric conductor and surrounded by an insulating material sheath and connected, at one end of the lead, to a connection head removable from the pacemaker and, at the other end, to a stimulation electrode device, said lead being characterized in that at a defined position of the flexible cord said sheath has an interruption of continuity making said spiralled conductor accessible from the outside, said interruption of continuity being able to be sealingly insulated from the outside by a mobile means.

In the present description by flexible cord is meant the connection between the stimulation electrode device and the pacemaker, whether this connection is formed of a single flexible cord or a flexible cord connected by any interconnection means to a so-called adapter connection having an appropriate head, the device of the invention being situated on the single flexible cord or on said connection.

In a preferred embodiment, said interruption of continuity is formed by a local absence, at least partial, of the sheath for baring the spiralled conductor, this acess to the conductor being masked by a sleeve mounted for sliding on the flexible cord.

With such a device, at the time of changing the pacemaker, said sleeve, which masks the orifice giving access to the internal conductor of the lead during use thereof, is slid so as to free said access for inserting a connection plug therein, such as a clip, in contact with said conductor. After connection of an auxiliary stimulation through this connection, the lead may be disconnected from the pacemaker without any risk.

Once the new pacemaker is positioned, the auxiliary connection clip is disconnected and the insulating and sealed sleeve is repositioned over said access. Thus, the cardiac stimulation of the patient is permanently ensured during the whole operation.

BRIEF DESCRIPTION OF THE DRAWINGS

Other characteristics and advantages will be clear from the following description of embodiments of the device of the invention, which description is given by way of example only and with reference to the accompanying drawings in which:

FIG. 1 is an axial sectional view of a flexible cord in accordance with the invention, in a first embodiment;

FIG. 2 illustrates a variant of the device of FIG. 1; and

FIG. 3 is an axial sectional view of a second embodiment.

DESCRIPTION OF THE PREFERRED EMBODIMENTS

In FIG. 1, a pacemaker has been shown schematically and partially at 1 in which is engaged the head 2 of an unipolar lead formed, in a way known per se, of an electric conductor 3 wound in a spiral with substantially jointing turns and surrounded by a sheath 4 made from a flexible electrically insulating and biocompatible material such as polyurethane.

Conductor 3 is extended, at the level of head 2, by a female tubular socket 5 intended to come into electric contact with the internal circuits of pacemaker 1 via a screw 6 for fixing the head.

The other end of conductor 3 is connected to the unipolar or bipolar electrode stimulation device (not shown).

According to the invention, at a given position of sheath 4, preferably close to head 2, an interruption of continuity is provided making the internal conductor 3 accessible.

In the embodiment illustrated in FIG. 1, this interruption of continuity consists in a local absence 7 of sheath, preferably over the whole periphery of the flexible cord, which thus has a narrow annular zone for temporarily connecting to conductor 3, for example, a crocodile type clip (not shown), itself connected to an external auxiliary stimulator for momentarily taking over from the pacemaker when this latter is disconnected for pacemaker replacement.

In normal use of the lead, with pacemaker 1 connected, the uncovered zone 7 of the sheath is masked and covered by means of a sleeve 8 in the form of an olive mounted for sliding on the flexible cord. In FIG. 1 the "normal" position of the sleeve, astride said zone 7, has been shown with broken lines at 8'.

The role of sleeve 8, made for example from the same material as sheath 4, is to insulate the bared portion of conductor 3 electrically and sealingly from the medium surrounding the lead. In the absence of such a sleeve, because pacemaker 1 and the proximal portion of the flexible cord are disposed under the skin of the patient and are likely to be in contact with a conducting medium, short circuits might occur between the spiralled conductor 3 and the pacemaker, which should be avoided at all costs.

Sleeve 8 must be relatively easy to slide along the flexible cord therefore, in order to have sealing as perfect as possible, on sheath 4, on each side of zone 7, annular projections 9 are advantageously provided slightly compressed by sleeve 8 when it is in its normal position (8') for insulating the auxiliary stimulation pole formed in zone 7. To have a better electric contact and avoid damaging the spiralled conductor 3, the bared portion of the latter is preferably, as illustrated in FIG. 2, surrounded by a metal conducting ring 10 welded to the conductor. It is in fact important to keep the spiralled form of conductor 3 for the internal passage of the conductor serves for introducing a guide for inserting the lead into the heart or repositioning the lead.

FIG. 3 shows another way of providing an interruption of continuity in sheath 4 surrounding the conductor 3 giving access to the latter. In this other embodiment, a branch is formed, for example in the form of a Y, with a spiralled conductor section 11 one of whose ends is welded to conductor 3 and the other end of which is welded to a connecting plug 12, male or female, which is accessible for a connecting plug, crocodile clip or the like, connected to an external auxiliary sitmulator.

Said section 11 and at least a portion of the auxiliary connection plug 12 are surrounded by an insulating sheath 4'.

The accessible part of plug 12 is capped by a cap 13 insulating it completely electrically and sealingly. The cap is for example made from the same material as sheaths 4,4'.

Cap 13, force fitted, is removed for changing the pacemaker for connecting the external auxiliary stimulator just before disconnection of head 2.

Cap 13 is repositioned after reconnection of head 2 in the pacemaker.

The device of the invention makes it possible, in all safety and particularly for dependent patients, to disconnect the head 2 from its pacemaker 1 for pacemaker replacement in particular but also for repositioning the lead in the heart by means of the guide whose progression inside the spiralled conductor 3 is in no wise hindered by the provision of the auxiliary stimulation pole of the invention.

The invention also applies to bipolar leads. In this case, the solution illustrated in FIG. 3 is used preferably, which means providing two branches side by side each assigned to one of the two spiralled conductors of the bipolar lead.

In the case where the device of the invention is provided on a connector or adapter connection, in patients fitted with a single flexible cord, in particular, it is possible to insert such a connection between their flexible cord and the pacemaker, the male connection head of the connection being identical or not to the head of said lead for connecting this latter to the same type of pacemaker or to a pacemaker with a different type of connection. Thus, it is not necessary to replace the existing lead which may thus, through the connection equiped with the invention, remain under stimulation at each subsequent change of pacemaker.

Finally, the invention is obviously not limited to the embodiments shown and described above but covers on the contrary all variants thereof, particularly in so far as the means are concerned giving access to the spiralled conductor 3 and the mobile means combined with said access means for providing access at will to said conductor or on the contrary total electric and sealed insulation thereof with respect to the environment in which the lead is plunged.

What is claimed is:

1. A pacemaker lead, comprising:
    a flexible cord having at least one spiralled electric conductor and a main sheath of insulating material surrounding said conductor;
    first connection means, located at one end of said cord, for removably coupling said conductor to a pacemaker;
    second connection means, located at an opposite end of said cord, for coupling said conductor to an electrode stimulation device;
    a preformed opening in said sheath between said ends of said cord; and
    a closure member coupled to said sheath for movement between an open position in which said closure member is spaced from said opening to expose and provide access to said conductor, and a closed position in which said closure member sealingly closes and insulated said opening from a surrounding environment.

2. A pacemaker leak according to claim 1 wherein
    said opening comprises at least a partial absence of said sheath baring a portion of said conductor and defining an access zone; and
    said closure member comprises a sleeve slidably mounted on said cord.

3. A pacemaker lead according to claim 2 wherein said sheath comprises annular sealing projections on each side of said access zone, said sealing projections being compressed by said sleeve in said closed position.

4. A pacemaker lead according to claim 2 wherein said portion of said conductor exposed in said access zone is surrounded by a conducting ring fixed to said conductor.

5. A pacemaker lead according to claim 1 wherein
    said opening comprises a laterally extending conductor branch of said conductor, said branch having an end connection plug at a free end thereof;
    a branch sheath partially surrounds said branch and said end connection plug, and has an open end; and
    said closure member comprises a sealed insulating cap closing said open end of said branch sheath is said closed position of said cap.

6. A pacemaker lead according to claim 5 wherein said flexible cord comprises two spiralled electric conductors, each having one laterally extending branch, end connection plug, branch sheath and sealed insulating cap.

7. A pacemaker lead according to claim 1 wherein said second connection means comprises adaptor means for connecting said conductor to an existing lead on a patient.

* * * * *